US00PP35882P3

(12) United States Plant Patent
van Zoest

(10) Patent No.: US PP35,882 P3
(45) Date of Patent: Jun. 25, 2024

(54) ***CLEMATIS* PLANT NAMED 'ZO18179'**

(50) Latin Name: ***Clematis* hybrid**
Varietal Denomination: Zo18179

(71) Applicant: Jos van Zoest, Boskoop (NL)

(72) Inventor: Jos van Zoest, Boskoop (NL)

(73) Assignee: J.VAN ZOEST BEHEER B.V., Boskoop (NL)

( * ) Notice: Subject to any disclaimer, the term of this patent is extended or adjusted under 35 U.S.C. 154(b) by 15 days.

(21) Appl. No.: 18/225,125

(22) Filed: Jul. 22, 2023

(65) Prior Publication Data

US 2024/0065121 P1 Feb. 22, 2024

(30) Foreign Application Priority Data

Aug. 19, 2022 (QZ) ..... PBR 20221957

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of *Clematis* plant named 'Zo18179' that is characterized by its floriferous and long blooming habit; blooming in May to June and July to August in The Netherlands, its flowers that appear from the base to the top of the plant, its flowers that are violet in color with a purple axillary central band on each tepal, and its dark purple anthers.

3 Drawing Sheets

Botanical classification: *Clematis* hybrid.
Variety denomination: 'Zo18179'.

CROSS REFERENCE TO RELATED APPLICATIONS

This application claims priority to European Community Plant Variety Office (CPVO) Plant Breeder's Rights Application No. 2022/1957 filed on Aug. 19, 2022, the entire contents of which is incorporated by reference herein. The information for the plant breeders' rights application was received directly from the Inventor. This application is also co-pending with a U.S. Plant Patent Application filed for a plant derived from the same breeding program that is entitled *Clematis* Plant Named 'Zo18197' (U.S. Plant Patent Pending 18/225,125).

BACKGROUND OF THE INVENTION

The present invention relates to a new and distinct cultivar of *Clematis* plant of hybrid origin and will be referred to hereafter by its cultivar name 'Zo18179'. 'Zo18179' is an herbaceous perennial grown for use as a landscape plant.

'Zo18179' originated as a seedling that arose from seed planted from open pollination of an unnamed and unpatented plant of *Clematis* from the Inventor's breeding program, reference no. 19960173, in August of 2018. The male parent is unknown. The new *Clematis* was selected as a single unique plant in June of 2019 from the resulting seedlings.

Asexual propagation of the new cultivar was first accomplished by softwood stem cuttings under the direction of the Inventor in June of 2019 in Boskoop, The Netherlands. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo18179' as a unique cultivar of *Clematis*.

1. 'Zo18179' exhibits a floriferous and long blooming habit; blooming in May to June and July to August in The Netherlands.
2. 'Zo18179' exhibits flowers that appear from the base to the top of the plant.
3. 'Zo18179' exhibits flowers that are violet in color with a purple axillary central band on each tepal.
4. 'Zo18179' exhibits dark purple anthers.

The female parent of 'Zo18179' differs from 'Zo18179' in having flowers that are smaller in size and light violet-blue in color with a central axillary red-purple band on each tepal, and a shorter flowering period. 'Zo18179' can be most closely compared to the *Clematis* cultivars 'Dr Ruppel' (not patented), 'Piilu' (not patented), and 'Zo18197'. All are similar to 'Zo18179' in having an axillary central band of color on the tepals. 'Dr Ruppel' differs from 'Zo18179' in having a more vigorous growth habit, a taller plant height, and flowers that have 6 tepals and appear only on the upper half of the plant. 'Piilu' differs from 'Zo18179' in having a more vigorous growth habit, a taller plant height, flowers that are more pink in color, and anthers that are creamy white in color. 'Zo18197' differs from 'Zo18179' in having flowers that are deep violet-blue in color with a lighter violet-blue band and anthers that are grey-green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium/groen-direkt, KVBC, Esveld Shop, AIPH, Plantago, Debloeimeesters, Facebook (Plantkeuze), Promesse de fleurs, J. van Zoest BV, dergartedbau, Jardin du Pic Vert, Camolin Potting Shed, FlorAccess, Jespers planteskole (facebook), Gabot, Horticulture Week, and Bloemenkrant.

BRIEF DESCRIPTION OF THE DRAWINGS

The accompanying color photographs illustrate the overall appearance and distinct characteristics of the new *Clematis*. The photographs were taken of a 15-month old plant as grown outdoors in a 13-cm container in Boskoop, The Netherlands.

The photograph in FIG. 1 provides a side view of 'Zo18179' in bloom.

Figure 1:
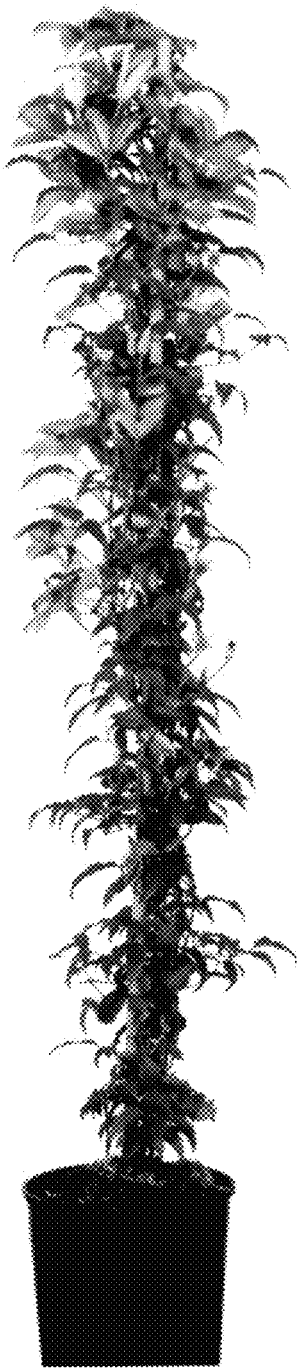
Figure 2:
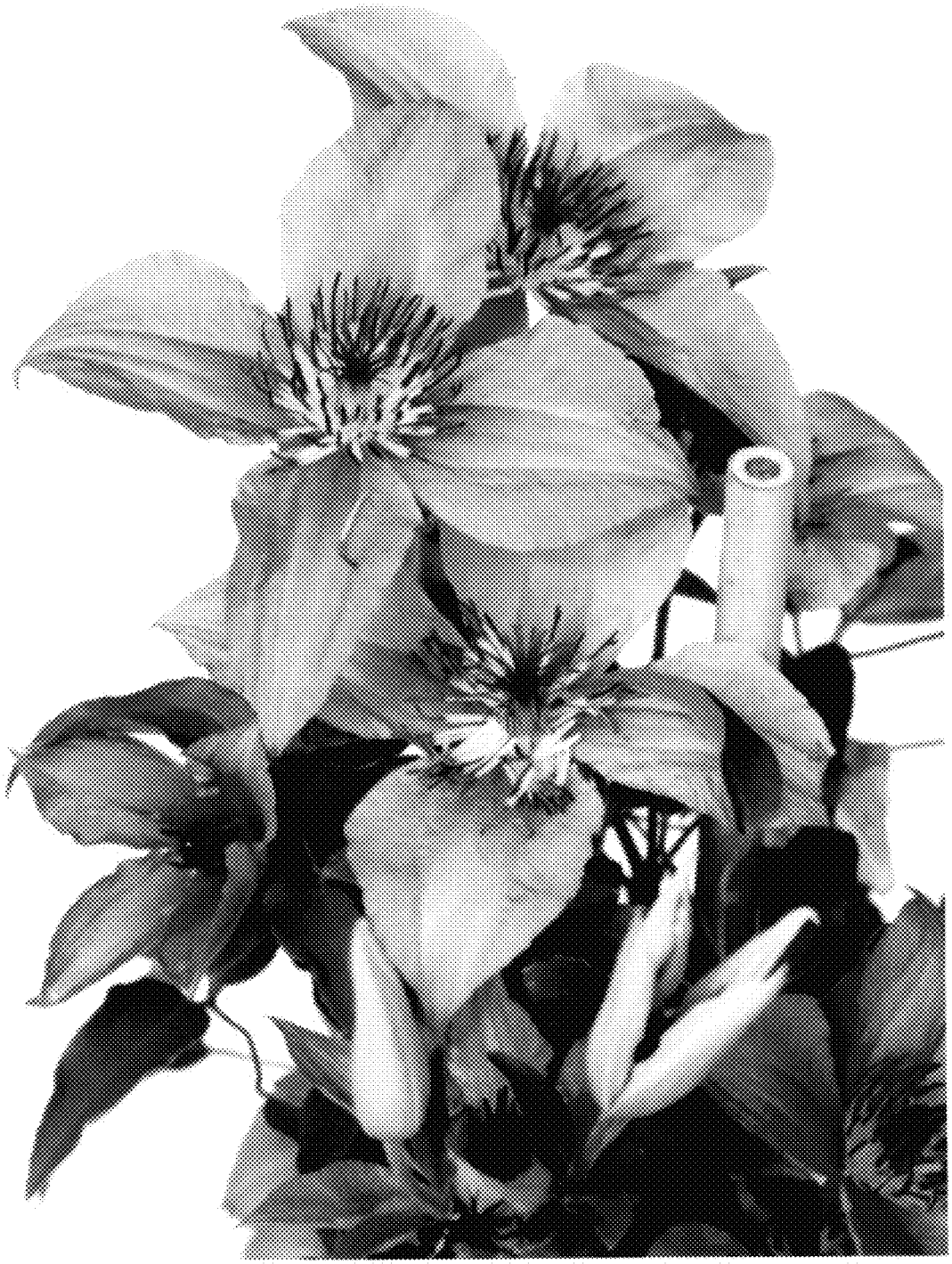

The photograph in FIG. 2 provides a close-up view of a flower of 'Zo18179'.

Figure 3:
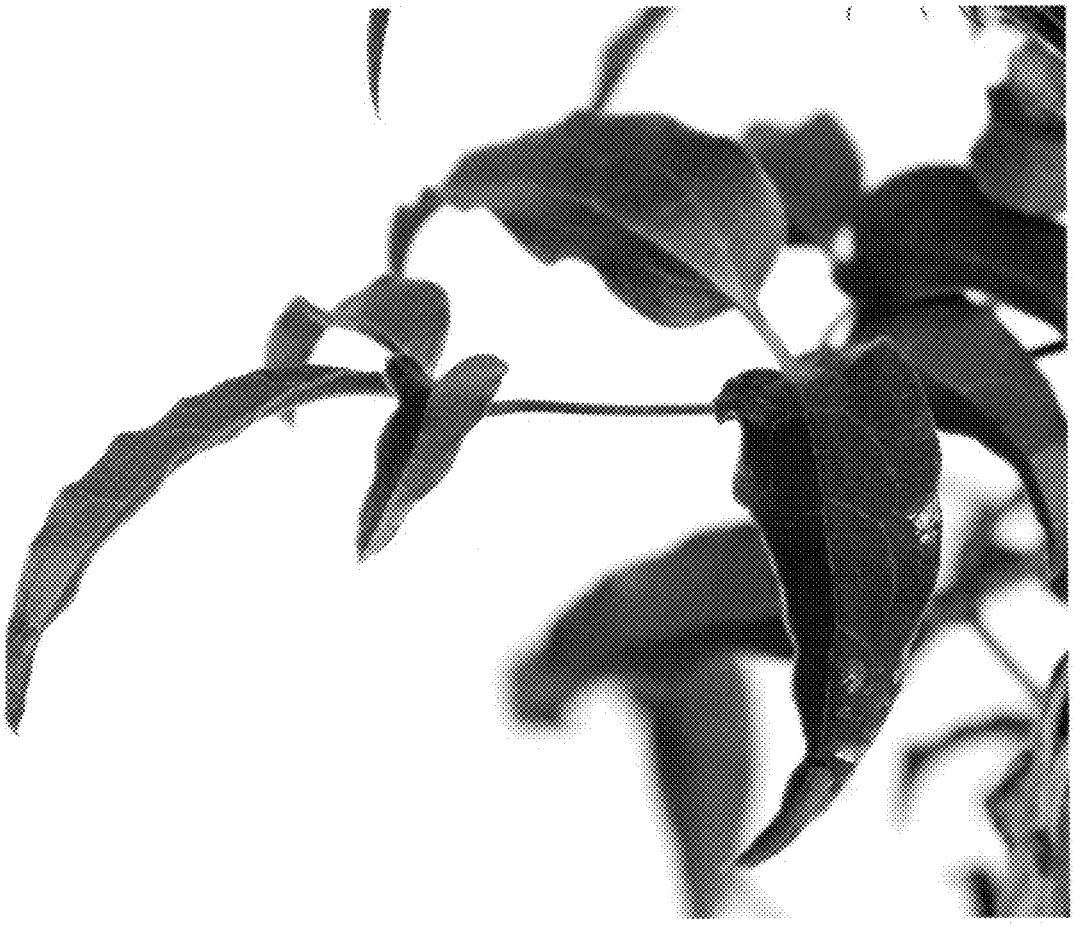

The photograph in FIG. 3 provides a close-up view of the foliage of 'Zo18179'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of 15-month old plants as grown outdoors in 13-cm containers in Boskoop, The Netherlands. The phenotype of the new cultivar may vary with variations in environmental, climatic, and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

*Blooming period*.—May to June and July to August in The Netherlands.

*Plant type*.—Deciduous woody perennial.

*Plant habit*.—Low growing climber (typically tied to trellis or cane) with blooms from the base to the top of the plant.

*Height and spread*.—Height; soil level to top of foliar plane 73.3 cm, soil level to top of floral plane 75.5 cm, diameter; 20 cm, as a 15-month old plant in a 13-cm container, up to 1.5 m in height when grown in the landscape.

*Hardiness*.—At least in U.S.D.A. Zones 6 to 10.

*Diseases and pests*.—No susceptibility or resistance to diseases or pests has been observed.

*Root description*.—Fleshy.

*Propagation*.—Softwood stem cuttings.

*Root development*.—An average of 6 to 8 weeks for root initiation and 5 months to produce a rooted cutting.

*Growth rate*.—Moderate.

Branch description:

*Branch shape*.—Angled.

*Branch color*.—Young; 144A to 144B, mature; 176A, internodes 148B to 148C, bark 200D.

*Branch size*.—Main branches; 67.2 cm in length, 2 mm in diameter, lateral branches; 1.9 cm in length, 1.75 mm in diameter.

*Branch surface*.—Young branches; densely covered with short adpressed hairs; 0.5 mm in length and 157D in color.

*Branch strength*.—Strong and flexible.

*Branch angle*.—Average of 80°.

*Branching*.—Average of 5 primary branches, 10 secondary branches per main branch.

*Internode length*.—Main stems; average of 6.3 cm, lateral stems; 1.9 cm.

Foliage description:

*Leaf arrangement*.—Opposite.

*Leaf division*.—Compound on main branch, single on lateral branches.

*Leaf quantity per plant*.—Main branch; 22 (11 pairs), lateral branch; 2 (1 pair).

*Leaf shape*.—Ovate to broadly ovate in outline, single leaves on lateral branches narrow ovate.

*Leaf base*.—Attenuate to nearly obtuse.

*Leaf apex*.—Narrowly acute.

*Leaf size*.—Average of 6.9 cm in length and 7 cm in width, single leaves on lateral branch; 2.3 cm in length, 9 mm in width.

*Leaflet quantity per compound leaf*.—Average of 5 on lower leaves and 3 on upper leaves.

*Leaflet shape*.—Narrowly ovate.

*Leaflet base*.—Attenuate to near obtuse.

*Leaflet apex*.—Narrowly acute.

*Leaflet venation*.—Pinnate, upper surface; 137A and NN137B, lower surface; 146B.

*Leaflet margins*.—Entire, slightly undulate, unlobed.

*Leaflet surface*.—Upper surface; glabrous, moderately glossy, lower surface; slightly to moderately glossy, moderately covered with soft pubescent hairs; 0.5 mm in length and N155A in color.

*Leaflet size*.—Average of 3.7 cm in length and 1.4 cm in width.

*Leaflet color*.—Young upper surface; 137B, young lower surface; a blend of 138A and 146B, mature upper surface a blend of 143A and 146A, mature lower surface 146B.

*Petioles*.—Average of 5.5 cm in length, 1 mm in diameter, strong, densely covered with short, adpressed pubescent hairs 0.5 mm in length, N155A in color, slightly glossy surface, color; upper surface N148A, lower surface 144A.

*Petiolules*.—Average of 3.5 mm in length, 1 mm in diameter, strong, densely covered with short, adpressed pubescent hairs 0.5 mm in length, N155A in color, slightly glossy surface, color; upper surface N148A, lower surface 144A.

Inflorescence description:

*Inflorescence type*.—Solitary.

*Inflorescence arrangement*.—Terminal on main stems and lateral stems.

*Peduncles*.—Average of 3.6 cm in length, 1.75 mm in diameter, color; 144A and 144B, surface is very slightly glossy, strong, densely covered with short, adpressed pubescent hairs 0.5 mm in length, N155A in color.

*Pedicels*.—None observed.

*Flower buds*.—Upright to slightly outward, lanceolate in shape, 2.4 cm in length, 8 mm in diameter, color; 145A to 145B, surface is matte and densely covered with short, pubescent hairs 0.75 mm in length, 157D in color.

*Flower fragrance*.—None.

*Lastingness of the flowers*.—14 days, self-cleaning.

*Flower quantity*.—Freely flowering, average of 50 flowers and 10 flower buds per plant.

*Flower shape*.—Rotate.

*Flower aspect*.—Upright and slightly outward.

*Flower shape*.—Round and slightly star-shaped.

*Flower size*.—9.2 cm in diameter, 1.9 cm in depth.

*Tepal number*.—4, occasionally 5.

*Tepal shape*.—Elliptic, slightly curved downward and slightly carinate.

*Tepal aspect*.—Rotate.

*Tepal apex*.—Apiculate.

*Tepal base*.—Cuneate.

*Tepal margin*.—Entire, finely undulate to crinked.

*Tepal surface*.—Upper surface; very slightly glossy, velvety, lower surface; matte, densely covered with soft pubescent hairs; 0.5 mm in length, NN155A in color.

*Tepal color*.—When opening upper surface; N88C, margins N88D, central band N79D, top 148D, when opening lower surface; a blend of 85A and N88D, central band a blend of 145C and 145D, when fully open upper surface; N88C, margins a blend of N88D and 90D, central band N79D, top 85A, tip N79D, when fully open lower surface; 85B, central band N155B, tinged 85D.

*Tepal size*.—Up to 5 cm in length and an average of 3 cm in width.

*Perianth*.—9.2 cm in length, 1.9 cm in diameter, rotate in shape.

Reproductive organs:

*Gynoecium*.—Pistils; 45, 1.2 cm in length, stigma; pointed in shape, 0.5 mm in length, 0.3 mm in diameter, N186B in color, style; 9.5 mm in length, N186C, fading to 145C, ovary; 145C in color.

*Androecium*.—Stamens; 65, filaments; 9 mm in length, 145C in color, anthers; 5 mm in length, 1 mm in width, basifixed, narrow oblong in shape, and N77B in color, fading to 79A at maturity, pollen; N186A in color and low in quantity.

*Seed*.—No seed heads have been observed to date.

It is claimed:

1. A new and distinct cultivar of *Clematis* plant named 'Zo18179' as herein illustrated and described.

* * * * *